(12) United States Patent
Noll et al.

(10) Patent No.: US 8,296,106 B2
(45) Date of Patent: Oct. 23, 2012

(54) APPARATUS, METHOD AND COMPUTER-READABLE STORAGE MEDIUM FOR PROCESSING A SIGNAL IN A SPECTROMETER SYSTEM

(75) Inventors: Robert Noll, Fairfield, CT (US); Aaron Turner, Southbury, CT (US); Alexander Majewski, Fairfield, CT (US)

(73) Assignee: Goodrich Corporation, Charlotte, NC (US)

( * ) Notice: Subject to any disclaimer, the term of this patent is extended or adjusted under 35 U.S.C. 154(b) by 353 days.

(21) Appl. No.: 12/712,811

(22) Filed: Feb. 25, 2010

(65) Prior Publication Data

US 2011/0208480 A1 Aug. 25, 2011

(51) Int. Cl.
G06F 17/16 (2006.01)
G06F 17/40 (2006.01)
(52) U.S. Cl. ............ 702/189; 702/106; 702/75; 702/76; 250/339.07; 250/339.09
(58) Field of Classification Search ................ None
See application file for complete search history.

(56) References Cited

U.S. PATENT DOCUMENTS

| | | | |
|---|---|---|---|
| 2,779,230 A | 1/1957 | White | |
| 5,267,019 A | 11/1993 | Whittaker et al. | |
| 5,751,839 A * | 5/1998 | Drocourt et al. | 382/133 |
| 5,818,578 A | 10/1998 | Inman et al. | |
| 5,883,518 A | 3/1999 | Borden | |
| 5,903,358 A | 5/1999 | Zare et al. | |
| 5,966,019 A | 10/1999 | Borden | |
| 6,061,134 A * | 5/2000 | Jensen et al. | 356/451 |
| 6,348,683 B1 | 2/2002 | Verghese et al. | |
| 6,466,322 B1 | 10/2002 | Paldus et al. | |
| 6,486,474 B1 | 11/2002 | Owen et al. | |
| 6,500,618 B1 | 12/2002 | Woolard et al. | |
| 6,865,198 B2 | 3/2005 | Taubman | |

(Continued)

FOREIGN PATENT DOCUMENTS

WO  WO 03/005510 A1  1/2003

(Continued)

OTHER PUBLICATIONS

Armerding, W. et al., *Multipass Optical Absorption Spectroscopy: a Fast-Scanning Laser Spectrometer for the in situ Determination of Atmospheric Trace-Gas Components, in Particular OH*, Applied Optics, vol. 35, No. 21, (1996), pp. 4206-4219.

(Continued)

*Primary Examiner* — Hal Wachsman
(74) *Attorney, Agent, or Firm* — Smith Moore Leatherwood LLP

(57) ABSTRACT

A method is provided that includes receiving and processing a sample signal scan. Processing the sample signal scan includes applying an inner-product operation on the sample signal scan and each of a plurality of eigenvectors to generate a plurality of corresponding coefficients, and subtracting the sample signal scan from a linear combination of the eigenvectors and corresponding coefficients to thereby produce a corrected sample signal scan. In this regard, the eigenvectors have been generated by decomposing a plurality of background reference signal scans according to a singular value decomposition technique. The signal scans include a plurality of electromagnetic signal measurements at a discrete set of frequencies, where each measurement has been taken by a spectrometer system passing an electromagnetic signal through a sample cell including just a base medium (for the background reference signal scans), or both a base medium and a sample medium (for the sample signal scan).

18 Claims, 4 Drawing Sheets

U.S. PATENT DOCUMENTS

| | | | |
|---|---|---|---|
| 7,174,037 | B2 | 2/2007 | Arnone et al. |
| 7,271,594 | B2 | 9/2007 | Abreu et al. |
| 7,291,839 | B1 | 11/2007 | Demers et al. |
| 7,352,463 | B2 | 4/2008 | Bounaix |
| 2002/0067480 | A1 | 6/2002 | Takahashi |
| 2004/0114939 | A1 | 6/2004 | Taylor |
| 2010/0074626 | A1* | 3/2010 | Majewski et al. ............ 398/141 |

FOREIGN PATENT DOCUMENTS

WO    WO 2004/083796 A1    9/2004

OTHER PUBLICATIONS

Auton, J. P., *Infrared Transmission Polarizers by Photolithography*, Applied Optics, vol. 6, No. 6, (1967), pp. 1023-1027.

Blickensderfer, R. P. et al., *A Long Path, Low Temperature Cell*, Applied Optics, vol. 7, No. 11, (1968), pp. 2214-2217.

Brown, E. R. et al., *Coherent Millimeter-Wave Generation by Heterodyne Conversion in Low-Temperature-Grown GaAs Photoconductors*, J. Appl. Phys., 73(3), (1993), pp. 1480-1484.

Edwards, T. H., *Multiple-Traverse Absorption Cell Design*, Journal of the Optical Society of America, vol. 51, No. 1, (1961), pp. 98-102.

Engel, G. S. et al., *Precise Multipass Herriott Cell Design: Derivation of Controlling Design Equations*, Optics Letters, vol. 32, No. 5, (2007), pp. 704-706.

Engeln, R. et al., *Phase Shift Cavity Ring Down Absorption Spectroscopy*, Chemical Physics Letters, 262, (1996), pp. 105-109.

Gregory, I. S. et al., *Resonant Dipole Antennas for Continuous-Wave Terahertz Photomixers*, [online] [retrieved May 24, 2010]. Retrieved from the Internet: <URL: http://adsabs.harvard.edu/abs/2004ApPhL..85.1622G>. 1 page.

Harmon, S. A. et al., *Part-Per-Million Gas Detection From Long-Baseline THz Spectroscopy*, Applied Physics Letters, vol. 85, No. 11, (2004), pp. 2128-2130.

Hayden, A. et al., *Determination of Trace-Gas Amounts in Plumes by the Use of Orthogonal Digital Filtering of Thermal-Emission Spectra*, Applied Optics, vol. 35, No. 16, (1996), pp. 2802-2809.

Herbelin, J. M. et al., *Sensitive Measurement of Photon Lifetime and True Reflectances in an Optical Cavity by a Phase-Shift Method*, Applied Optics, vol. 19, No. 1, (1980), pp. 144-147.

Lehmann, K. K. et al., *The Superposition Principle and Cavity Ring-Down Spectroscopy*, J. Chem. Phys., vol. 105, No. 23, (1996), pp. 10263-10277.

McCubbin, Jr., T. K. et al., *A White-Type Multiple-Pass Absorption Cell of Simple Construction*, Applied Optics, vol. 2, No. 7, (1963), pp. 764-765.

Mouret, G. et al., *THz Media Characterization by Means of Coherent Homodyne Detection, Results and Potential Applications*, Appl. Phys., B89, (2007), pp. 395-399.

Pickett, H. M. et al., *A New White Type Multiple Pass Absorption Cell*, Applied Optics, vol. 9, No. 10, (1970), pp. 2397-2398.

Rayl, G. J., *Multiple Traversal Absorption Cell of Minimum Volume: Design*, Applied Optics, vol. 15, No. 4, (1976), pp. 921-928.

Robert, C., *Simple, Stable, and Compact Multiple-Reflection Optical Cell for Very Long Optical Paths*, Applied Optics, vol. 46, No. 22, (2007), pp. 5408-5418.

Scherer, J. J. et al., *Cavity Ringdown Laser Absorption Spectroscopy: History, Development, and Application to Pulsed Molecular Beams*, Chem. Rev., 97, (1997), pp. 25-51.

Ulrich, P. et al., *Variable Metal Mesh Coupler for Far Infrared Lasers*, Applied Optics, vol. 9, No. 11, (1970), pp. 2511-2516.

Verghese, S. et al., *Highly Tunable Fiber-Coupled Photomixers with Coherent Terahertz Output Power*, IEEE Transactions on Microwave Theory and Techniques, vol. 45, No. 8, (1997), pp. 1301-1309.

Verghese, S. et al., Generation and Detection of Coherent Terahertz Waves Using Two Photomixers, Applied Physics Letters, vol. 73, No. 26, (1998), pp. 3824-3826.

Verghese, S. et al., *The Photomixer Transceiver*, Invited Paper, SPIE Conference on Terahertz Spectroscopy and Applications, San Jose, CA, Jan. 1999, pp. 7-13.

White, J. U., *Very Long Optical Paths in Air*, J. Opt. Soc. Am., vol. 66, No. 5, (1976), pp. 411-416.

Zalicki, P. et al., *Cavity Ring-Down Spectroscopy for Quantitative Absorption Measurements*, J. Chem. Phys., 102 (7), (1995), pp. 2708-2717.

U.S. Appl. No. 12/712,736, filed Feb. 25, 2010; In re: Majewski et al., entitled *System and Method for Magnitude and Phase Retrieval by Path Modulation*.

A. E. Siegman, Lasers, pp. 435-437, University of Science Books, Mill Valley, California 1986.

* cited by examiner

APPARATUS, METHOD AND COMPUTER-READABLE STORAGE MEDIUM FOR PROCESSING A SIGNAL IN A SPECTROMETER SYSTEM

FIELD OF THE INVENTION

Exemplary embodiments of present invention generally relate to spectrometer systems and methods of propagating electromagnetic signals and, more particularly, an apparatus, method and computer-readable storage medium for processing a signal in a spectrometer system.

BACKGROUND OF THE INVENTION

Spectrometry using continuous wave (CW) tunable sources with narrow spectral linewidth and long coherence lengths has well-known advantages associated with high spectral contrast, frequency selectivity and excellent sensitivity. Scanning CW terahertz (THz) spectrometers are a prime example of this technology. In such systems, phase stability in the transmitter-to-receiver demodulation processing may be required to obtain an accurate measurement of the transmitted electric-field intensity and to characterize any resulting absorption losses from samples in the spectrometer. However, the signal generated by a THz spectrometer may contain a strong background signature created by superimposed standing wave patterns within the spectrometer cavity or sample cell.

As the path length of the spectrometer increases, the variation in amplitude as a function of measurement wavelength may also increase in frequency. A spectrometer acquiring data at a discrete set of THz frequencies, then may under sample the background pattern. The resulting background signature may be an aliasing of the actual standing wave structure within the instrument, and change shape and amplitude as the measurement frequency sampling is altered.

In the presence of small frequency calibration drifts occurring in a scanning spectrometer, the sensitivity of the background structure to frequency sampling may cause changes in that structure over multiple measurements. This variation in the background between scans may reduce the effectiveness of a simple ratio technique—dividing a measurement by a reference taken with no sample present—to accurately determine the spectral features of a sample being tested.

SUMMARY OF THE INVENTION

In light of the foregoing background, embodiments of the present invention provide an improved apparatus, method and computer-readable storage medium for processing a signal in a spectrometer system. According to one aspect of the present invention, a method is provided that includes receiving and processing a sample signal scan. Processing the sample signal scan includes applying an inner-product operation on the sample signal scan and each of a plurality of eigenvectors to generate a plurality of corresponding coefficients, and subtracting the sample signal scan from a linear combination of the eigenvectors and corresponding coefficients to thereby produce a corrected sample signal scan. In this regard, the eigenvectors have been generated by decomposing a plurality of background reference signal scans according to a singular value decomposition technique; and as such, the method may also include receiving and decomposing the plurality of background reference signal scans to generate the eigenvectors.

The signal scans include a plurality of electromagnetic signal measurements at a discrete set of frequencies, where each measurement has been taken by a spectrometer system passing an electromagnetic signal through a sample cell including a base medium with (for the sample signal scan) or without (for the background reference signal scans) a sample medium.

The method may also include segmenting the sample signal scan into a plurality of frequency segments, processing the sample signal scan segments to produce a respective plurality of corrected sample signal scan segments, and assembling the corrected sample signal scan segments. For each sample signal scan segment, processing the sample signal scan segments may include applying an inner-product operation on the sample signal scan segment and a respective set of eigenvectors to generate a respective set of corresponding coefficients, and subtracting the sample signal scan segment from a linear combination of the respective set of eigenvectors and corresponding coefficients to thereby produce a respective corrected sample signal scan segment.

The aforementioned sets of eigenvectors may have been generated by segmenting a plurality of background reference signal scans into a plurality of sets of background reference signal scan segments, and decomposing each set of the background reference signal scan segments according to a singular value decomposition technique. Thus, the method may also include receiving and segmenting the plurality of background reference signal scans into a plurality of sets of background reference signal scan segments, and decomposing each set of the background reference signal scan segments to generate the plurality of sets of eigenvectors.

The method may further include identifying an electromagnetic signal measurement in the sample signal scan corresponding to an electromagnetic signal measurement in the corrected sample signal that exceeds a specified absorption threshold. The method may then include removing the identified electromagnetic signal measurement to produce a modified sample signal scan, and processing the modified sample signal scan. In such an instance, processing the modified sample signal scan may include applying an inner-product operation on the modified sample signal scan and each of a plurality of eigenvectors to generate a second plurality of corresponding coefficients, and subtracting the sample signal scan from a linear combination of the eigenvectors and second corresponding coefficients to thereby produce a further corrected sample signal scan.

Moreover, the method may include calculating a ratio of the sample signal scan to an average of the background reference signal scans, and adjusting the corrected sample signal scan based on the ratio.

According to other aspects of the present invention, an apparatus and computer-readable storage medium for processing a signal in a spectrometer system are provided. Exemplary embodiments of the present invention therefore provide an improved apparatus, method and computer-readable storage medium for processing a signal in a spectrometer system. As indicated above, and explained below, exemplary embodiments of the present invention may solve problems identified by prior techniques and provide additional advantages.

BRIEF DESCRIPTION OF THE DRAWINGS

Figure 1:
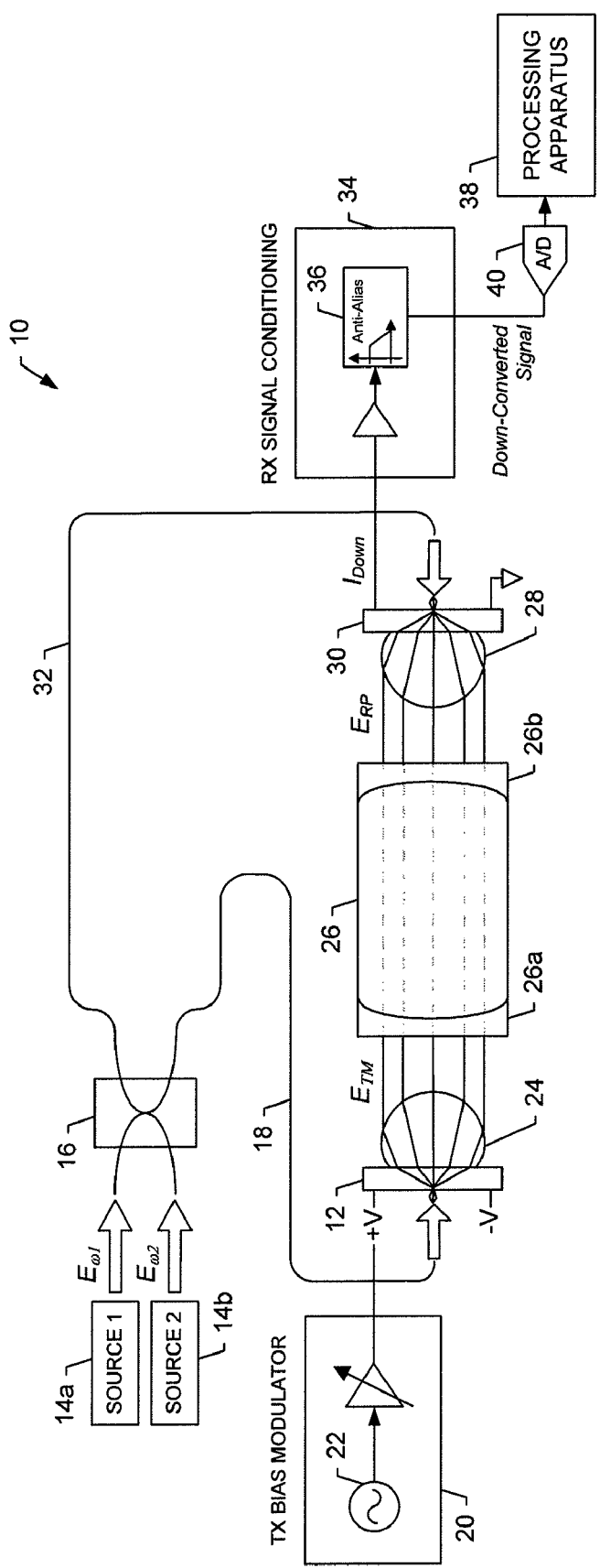
Figure 2:
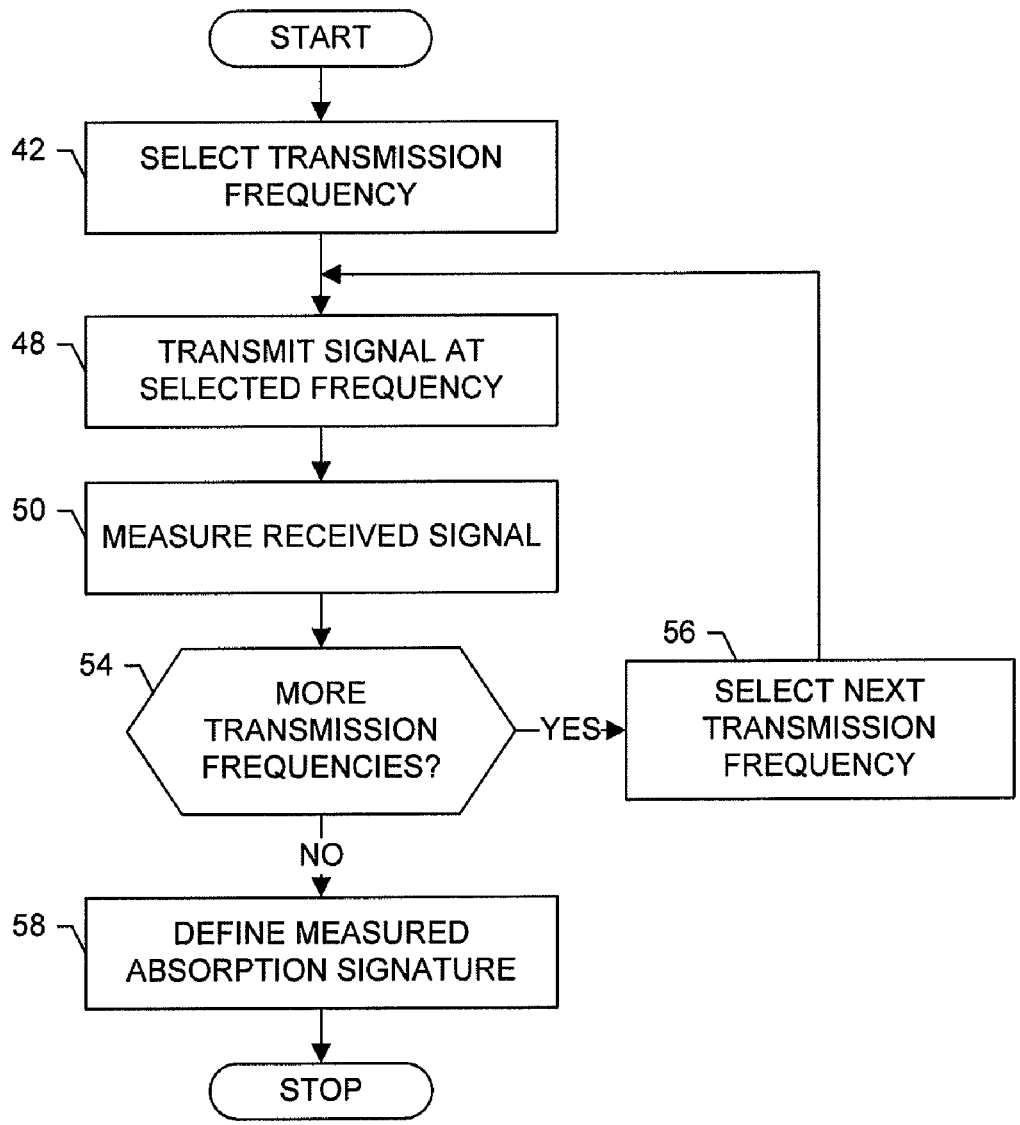
Figure 3:
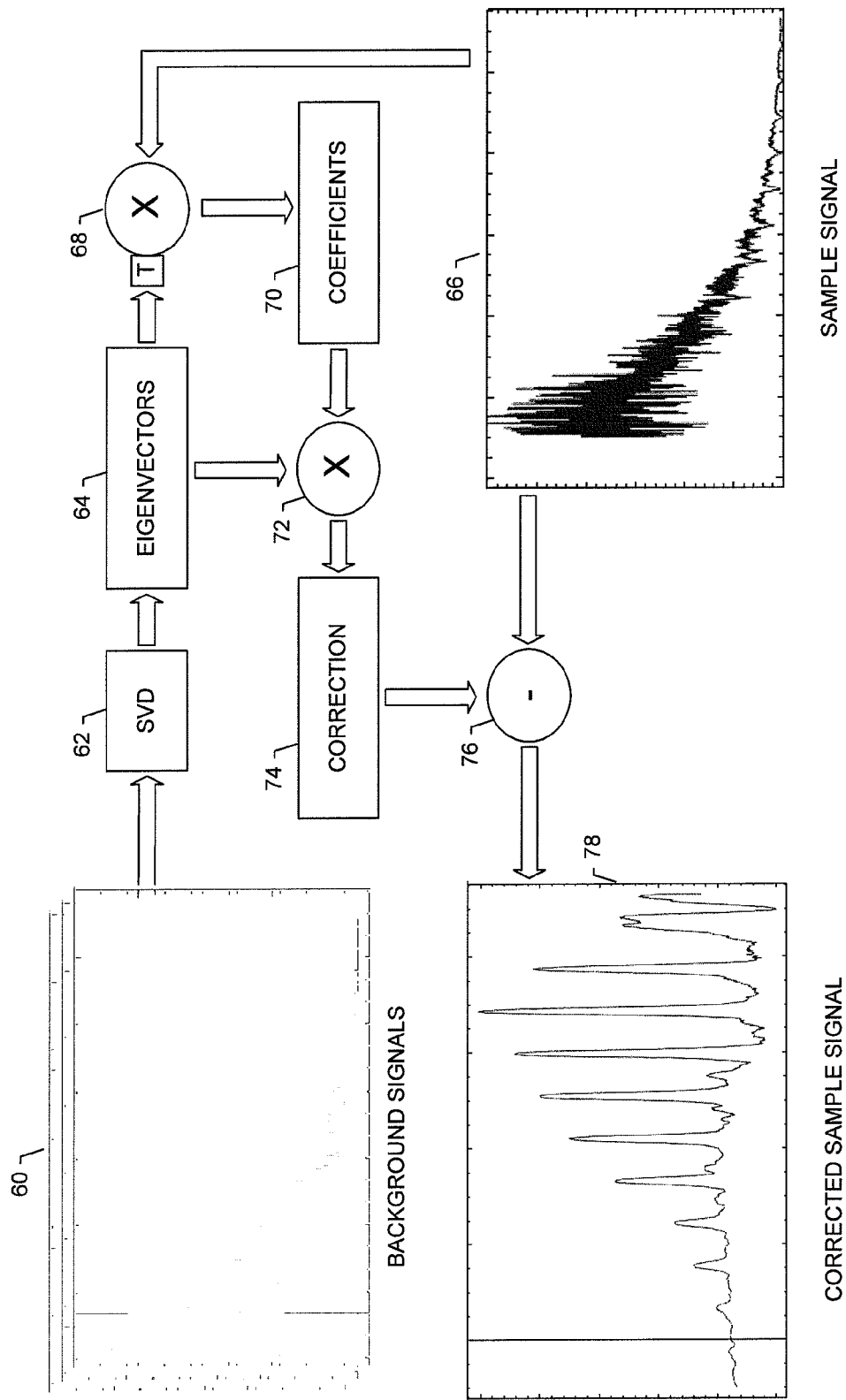
Figure 4:
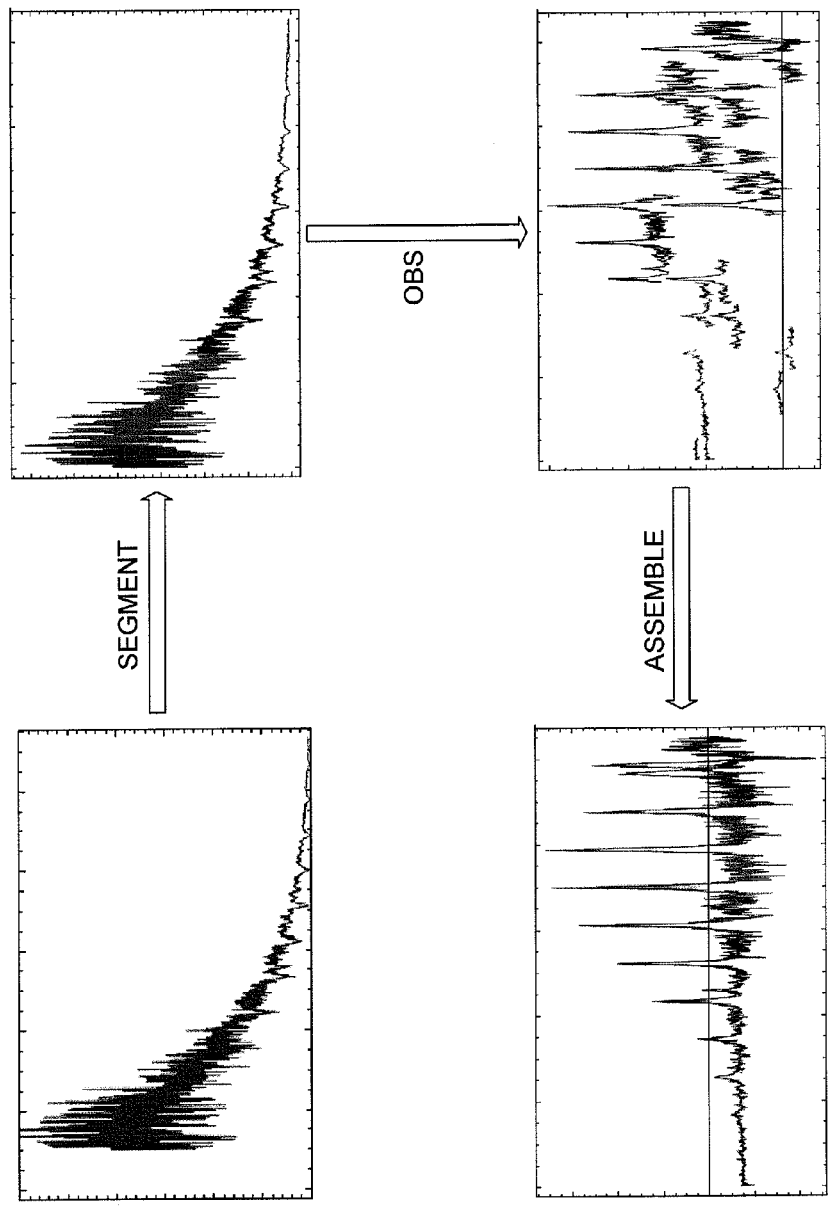

Having thus described the invention in general terms, reference will now be made to the accompanying drawings, which are not necessarily drawn to scale, and wherein:

FIG. 1 is a schematic block diagram of a spectrometer system in accordance with one exemplary embodiment of the present invention;

FIG. 2 is a flowchart illustrating various steps in a method of sweeping a spectrometer system through a frequency spectrum, according to exemplary embodiments of the present invention; and FIGS. 3 and 4 are block diagrams illustrating operations that a processing apparatus may be configured to perform according to exemplary embodiments of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In this regard, reference may be made herein to a number of mathematical or numerical expressions that may be related by equality. It should be understood, however, that this equality may refer to an absolute or approximate equality, such that exemplary embodiments of the present invention may account for variations that may occur in the system and method, such as those due to engineering tolerances. Further, although a number of variables may be reflected by mathematical symbols including subscripts at various instances, it should be understood that these symbols and subscripts are presented solely for illustrative purposes, and should not be construed as limiting the scope of the invention. Like numbers refer to like elements throughout.

FIGS. 1 and 2 illustrate a spectrometer system and method that may benefit from exemplary embodiments of the present invention ("exemplary" as used herein referring to "serving as an example, instance or illustration"). It should be understood, however, that the spectrometer system and method illustrated and hereinafter described are merely illustrative of one type of system and method that may benefit from exemplary embodiments of the present invention and, therefore, should not be taken to limit the scope of the present invention. For an example of another spectrometer system and method that may benefit from exemplary embodiments of the present invention is described in U.S. patent application Ser. No. 12/712,736, entitled: System and Method for Magnitude and Phase Retrieval by Path Modulation, filed Feb. 25, 2010. The content of the '736 application is hereby incorporated by reference in its entirety.

While several embodiments of the spectrometer system and method are illustrated and will be hereinafter described for purposes of example, other types of systems and methods of propagating electromagnetic signals may readily employ the present invention. Moreover, the system and method of the present invention will be primarily described in conjunction with signals in the THz (or mmW) region of the electromagnetic spectrum. But the system and method of embodiments of the present invention may be utilized in conjunction with a variety of other applications, both within and outside the THz region of the electromagnetic spectrum.

As shown, a spectrometer system 10 of one exemplary embodiment of the present invention includes a transmitter 12 configured to transmit a beam of coherent radiation (electromagnetic wave) at a given frequency. The transmitter can comprise any of a number of different transmitters known to those skilled in the art. In one exemplary embodiment, for example, the transmitter comprises a photomixer transmitter. In such instances, the transmitter includes a high-speed photoconductive diode (i.e., photomixer), which may be pumped with two laser sources 14a, 14b via a beam combiner/splitter 16 and an optically coupled first optical path 18 (e.g., optical fiber). In this regard, the laser sources may be configured to emit signals with electric fields having offsetting frequencies at $\omega_1$ and $\omega_2$ (i.e., $E_{\omega 1}$ and $E_{\omega 2}$). Also note that frequencies $\omega_1$ and $\omega_2$ may be expressed as angular frequencies, or as corresponding temporal frequencies ($f=\omega/2\pi$).

The transmitter 12 may be coupled to a transmitter bias modulator 20 including a voltage source 22 configured to generate a sinusoidal modulated voltage with which the photomixer of the transmitter may be biased, although it should be understood that the system need not frequency modulate the signal. By locating the photomixer at the driving point of an antenna, such as a spiral, dipole or slot antenna, the difference-frequency current is converted to difference-frequency photons. The result is a highly-tunable, continuous-wave (CW), highly-coherent source of radiation contained in a single (quasi-Gaussian) spatial mode, and having a transmitted electric field $E_{TM}$. For more information on such a transmitter, see U.S. Pat. No. 6,348,683 entitled: Quasi-Optical Transceiver Having an Antenna with Time Varying Voltage, issued Feb. 19, 2002.

Thus, the method of one exemplary embodiment includes selecting a transmission frequency, thereafter transmitting a beam of radiation (i.e., source beam) at that frequency from the transmitter 12, as shown in blocks 42 and 48 of FIG. 2. The transmission frequency can be selected in any of a number of different manners. To detect a sample based upon a measured absorption signature, however, the transmission frequency may be typically selected within a range of frequencies over which the absorption signature is defined. In a photomixer transmitter, then, the photomixer can be pumped with tunable laser sources at a frequency $\omega_2$, and a frequency $\omega_1$ that are selected to thereby select the difference, or transmission, frequency (i.e., $\omega_2-\omega_1$).

The beam of radiation from the transmitter 12 may pass through a collimating lens 24 to produce a collimated beam of radiation. The beam may then pass through a sample cell 26 that may be bounded by reflectors 26a and 26b through which the beam passes, and that may include a sample medium to be analyzed and a base medium, such as ambient air. As will be appreciated, the sample and base medium can have any of a number of different forms through which the beam of radiation is at least partially transmissive. For example, the sample and base medium can comprise a solid, liquid, gas, plasma or aerosol. More particularly, in various advantageous embodiments, the base medium of ambient air may be in gas form, while a sample may be in gas or aerosol form.

As the beam of radiation passes through the sample cell 26, the sample and base medium in the sample cell absorb at least a portion of the beam, or more particularly at least a portion of the electric field of the beam. The remaining, unabsorbed portion of the beam of radiation (i.e., received signal) then exits the sample cell. The sample signal then propagates to a focusing lens 28, from which the focused signal is picked up or otherwise received by a receiver 30 as a received signal $E_{RP}$.

The receiver obtains a measurement representative of the received electric field $E_{RP}$, as shown in block 50 of FIG. 2. Similar to the transmitter 12, the receiver may comprise an electric-field detector such as a photomixer receiver (homodyne receiver). The photomixer receiver may include an antenna configured to receive the electric field and generate a corresponding voltage in response thereto, which may be directed to a high-speed photoconductor. The photoconductor is also electrically coupled to a second optical path 32 for pumping the photoconductor with beams from the same two laser sources 14a, 14b pumping the photomixer transmitter 12. In this regard, the beam combiner/splitter 16 may separate each of the signals from the laser sources into the aforementioned first optical path 18, as well as another, second optical path (e.g., optical fiber) for pumping the receiver photomixer. These signals, then, may modulate a conductance of the photomixer.

The voltage generated by the receiver antenna may be applied to the photomixer active material, and produce a current through the modulated conductance. The difference frequency result of the product is the down-converted signal current $I_{Down}$, which may have a corresponding down-converted electric-field $E_R$, either or both of which may constitute or otherwise represent a signal. For more information on such a receiver, see the aforementioned '683 patent.

The down-converted signal current $I_{Down}$ and/or electric-field $E_R$ may be applied to receiver signal conditioning circuitry 34 including, for example, an anti-aliasing filter 36. The output of the signal conditioning circuitry may then be input to a processing apparatus 38, such as for performing digital signal processing operations thereon. In this regard, the processing apparatus can comprise any of a number of different devices configured to operate in accordance with exemplary embodiments of the present invention. For example, the processing apparatus may comprise a computer (e.g., personal computer, laptop computer, server computer, workstation computer) or other computing apparatus. The processing apparatus may include a processor and computer-readable storage medium. The processor may include, for example, one or more programmed or programmable general-purpose processors, microprocessors, coprocessors, controllers, specialized digital signal processors and/or various other processing devices including one or more integrated circuits (e.g., ASICs, FPGAs), hardware accelerators, processing circuitry or the like.

The computer-readable storage medium of the processing apparatus 38 may include volatile and/or non-volatile memory, which may be embedded and/or removable, and may include, for example, read-only memory, flash memory, magnetic storage devices (e.g., hard disks, floppy disk drives, magnetic tape, etc.), optical disc drives and/or media, non-volatile random access memory (NVRAM), and/or the like. The computer-readable storage medium may store any of a number of different data, content or the like, according to exemplary embodiments of the present invention. For example, the computer-readable storage medium may be configured to store executable or other computer-readable instructions that may be executed or otherwise processed by the processor.

If the spectrometer system 10 frequency modulates the signal, the signal processing operations performed by the processor 38 may include recovering the amplitude of the down-converted signal $E_R$ such as by an analog-to-digital converter (A/D) 40 direct sampling of the signal at the modulating frequency, and the processor Discrete Fourier Transformation (DFT) processing of the sampled data. Alternatively, for example, the spectrometer system may further include a synchronous demodulator such as a lock-in amplifier (not shown) for further processing the down-converted signal $E_R$. In this regard, such a synchronous demodulator may include a local oscillator operating at the modulating frequency $\omega_m$ to thereby recover the amplitude of the down-converted signal.

In operation as a spectrometer, the system 10 scans through a number of transmission frequencies in a range of frequencies, such as by pumping the photomixers of the transmitter 12 and receiver 30 with tunable laser sources at frequency $\omega_2$, and frequency $\omega_1$ that are scanned through a number of frequencies, as shown in blocks 54 and 56 of FIG. 2. For each transmission frequency in the range of frequency, and thus each beam of radiation having a different transmission frequency, the processor 38 may measure the amplitude and/or phase of the down-converted signal current $I_{Down}$. The resulting collection of transmissions amplitudes and/or phases, and associated transmission frequencies, may define a measured absorption or dispersion signature for the sample in the sample cell 26, from which the sample may be identified, as shown in block 58 of FIG. 2.

As explained in the background section, the signal generated by a spectrometer (e.g., THz spectrometer) may contain a strong background signature created by superimposed standing wave patterns within a sample cell (e.g., sample cell 26). As the path length of the spectrometer increases, the variation in amplitude as a function of measurement wavelength may also increase in frequency. A spectrometer acquiring data at a discrete set of THz frequencies over a spectrum of interest, then may under sample the background pattern. The resulting background signature may be an aliasing of the actual standing wave structure within the instrument, and change shape and amplitude as the measurement frequency sampling is altered.

As also explained in the background, in the presence of small frequency calibration drifts occurring in a scanning spectrometer, the sensitivity of the background structure to frequency sampling may cause changes in that structure over multiple measurements. This variation in the background between scans may reduce the effectiveness of a simple ratio technique—dividing a measurement by a reference taken with no sample present—to accurately determine the spectral features of a sample being tested.

In view of the foregoing, the processing apparatus 38 of exemplary embodiments of the present invention may be configured to process acquired measurement according to an orthogonal background subtraction or suppression (OBS) technique to at least partially separate a complex and varying background structure from an acquired measurement, and thereby reveal the spectrum of a sample under test. As described herein, the acquired measurements may be in the form of the down-converted electric-field (or signal) $E_R$ measured at a discrete set of frequencies in a spectrum of interest, but it should be understood that the measurements may equally be in the form of the down-converted signal current $I_{Down}$ measured over a similar discrete set of frequencies. As also described herein, the processing OBS technique may but need not be implemented in logarithm space so that division of a reference measurement is equivalent to subtraction.

Reference is now made to FIGS. 3 and 4, which illustrate block diagrams of operations that the processing apparatus 38 may be configured to perform according to exemplary embodiments of the present invention. The illustrated block diagrams include a number of scans to illustrate signals or measurements of signals received or calculated by the processing apparatus. It should be understood that references to a "signal" may be used interchangeably with references to a "measurement of a signal," as may be received by the processing apparatus. It should also be understood that the illustrated scans are presented merely for illustration, and that signals, measurements or other data may be received, calculated or presented in any of a number of different forms without departing from the spirit and scope of the present invention.

According to exemplary embodiments of the present invention, the processing apparatus 38 may be configured to process a signal scans by a process that includes obtaining or otherwise retrieving N background reference signal scans 60. As described herein, each a signal scan includes signal measurements at a discrete set of frequencies in a spectrum of interest. In the context of a background reference signal scan, each measurement is taken of a transmitted signal passing through the sample cell 26 with the base medium (e.g., ambient air) but without the sample medium. The processing apparatus may then be configured to decompose the background reference signal scans, such as in accordance with a singular value decomposition (SVD) technique 62, to generate a set of N orthogonal eigenvectors 64. The resulting eigenvectors may represent a set of basis functions as a function of frequency, whose linear combinations may reproduce each of the N background reference signal scans. The eigenvectors may then be utilized by the processing apparatus to process a subsequent sample signal scan. It should be understood that the background reference signal scans may be obtained and decomposed at any time prior to processing a sample signal. Consequently, the background reference signal scans or resulting eigenvectors may be stored in memory embodied within or otherwise associated with the processing apparatus, and retrieved at an appropriate time for use in generating the eigenvectors and/or processing a sample signal scan.

At some time after generating the eigenvectors 64, and with the sample medium having been inserted into the sample cell 26, a sample signal scan 66 may be obtained, where each measurement of the scan may be taken of a transmitted signal passing through the sample cell including the sample and base mediums. The processing apparatus 38 may be configured to receive and project the sample signal scan on each of the eigenvectors to generate corresponding coefficients 70. This projection may be accomplished, for example, by applying an inner-product (dot-product) operation 68 on the eigenvectors and sample signal scan, which itself may be accomplished by multiplying the transpose of the eigenvectors and sample signal scan. Regardless of the manner by which the sample signal scan is projected onto each of the eigenvectors, the eigenvectors may be linearly combined 72 with their corresponding coefficients to generate a correction value or values 74, which may be subtracted 76 from the sample signal scan to produce a corrected sample signal scan.

The OBS technique implemented by the processing apparatus 38 may reveal the content of the sample signal scan that is orthogonal to the space of spectra spanned by the background reference eigenvectors. The technique implemented by the processing apparatus may be able to remove a background signature including superimposed standing waves of time-varying amplitudes. In addition, consider that at terahertz, the gas spectra of interest may be spectral lines caused by the rotational characteristics of the molecule. The resolution of the spectrometer system of exemplary embodiments of the present invention may be sufficient to resolve many of these lines which may require sampling rich spectra with a large number of samples.

As will be appreciated, performing SVD on a set of N background reference signal scans 60, each with M measurement frequencies, may require the allocation and manipulation of an N×M matrix. A typical THz spectrum may include 10,000 to 100,000 measurement points (frequencies), and as many as 50 background reference signal scans may be acquired. As shown more particularly in FIG. 4, to relieve at least a portion of the otherwise high computing and storage resources that may otherwise be required to process such signal scans, the processing apparatus 38 of various example embodiments may be configured to segment, process and then stitch back together signal scans. More particularly, the processing apparatus may be configured to segment the background reference signal scans and sample signal scan 66 into a plurality of overlapping frequency segments, each of which may be individually processed such as in accordance with the OBS technique explained above with respect to FIG. 3. The overlapping spectra segments resulting from individually processing the segments may be assembled (or stitched together) and averaged, such as according to a least squares minimization of discrepancy technique with respect to spectra bias and tilt.

In implementing the OBS technique according to exemplary embodiments of the present invention, the processing apparatus 38 may be configured to apply a bias correction to any OBS residual. In this regard, in the generated eigenvectors 64 (or set of eigenvectors for each segment), the mean of the background may be represented as a linear combination of eigenvectors. As a result, the OBS technique implemented by the processing apparatus 38 may alter the mean of each segment. In addition, during the stitching reconstruction process, one segment may be held constant while the processing apparatus optimally recombines the others with respect to bias and tilt based on the segment being held constant. As a consequence, if not corrected, the absolute bias of the measured spectrum may be lost during this processing.

Accurate detection of broadband absorbing gas species may require that the absolute absorption magnitude be restored to the processed measurement. Thus, the processing apparatus 38 of exemplary embodiments of the present invention may be configured to calculate the ratio between the sample and background signals, and then set the average signal of the final spectrum to match this ratio, thereby correcting the bias due to any OBS residual. More particularly, for example, the processing apparatus may be configured to calculate the difference between the average sample signal and the average background signal—the averages performed over all frequencies. The processed final spectrum may then be adjusted so that its average over all frequencies matches the calculated difference. When these calculations are performed on the logarithms of the sample and background amplitudes, this has the effect of setting the average transmission of the processed data to the ratio of the sample signals to the background signals.

Even further, in the presence of high slopes in the sample signal spectrum, the projection of segments onto the corresponding eigenvectors can result in anomalously high coefficients 70, which in turn can result in a failure to accurately suppress the background signal in the segments containing the high slope features. To address this condition, the processing apparatus 38 of exemplary embodiments may employ the OBS technique in an iterative manner. For example, after initially processing a sample signal scan (see FIG. 3), data points in the sample signal scan corresponding to points in the corrected sample signal scan exceeding a specified absorption threshold may be identified and temporarily removed from the original sample signal scan. The modified raw sample signal scan may then be projected (e.g., applying the inner-product operation 68) a second time on to the eigenvectors to determine more-accurate coefficients. The resulting linear combination of eigenvectors with the more-accurate coefficients may then be subtracted from the original sample signal scan (including the high absorption points) to yield a further, more-accurate corrected sample signal scan.

According to one aspect of the example embodiments of present invention, the operations performed by the processing apparatus 38, such as those illustrated by the block diagrams of FIGS. 3 and 4, may be performed by various means. It will be understood that each block or operation of the block diagrams, and/or combinations of blocks or operations in the block diagrams, can be implemented by various means. Means for implementing the blocks or operations of the block diagrams, combinations of the blocks or operations in the block diagrams, or other functionality of example embodiments of the present invention described herein may include hardware, and/or a computer program product including a computer-readable storage medium having one or more computer program code instructions, program instructions, or executable computer-readable program code instructions stored therein. In this regard, program code instructions may be stored on a computer-readable storage medium and executed by a processor, such as those of the processing apparatus.

As will be appreciated, program code instructions may be loaded onto a computer or other programmable apparatus (e.g., processor, memory, or the like) from a computer-readable storage medium to produce a particular machine, such that the particular machine becomes a means for implementing the operations specified in the block diagrams' block(s) or operation(s). These program code instructions may also be stored in a computer-readable storage medium that can direct a computer, a processor, or other programmable apparatus to function in a particular manner to thereby generate a particular machine or particular article of manufacture. The instructions stored in the computer-readable storage medium may produce an article of manufacture, where the article of manufacture becomes a means for implementing the functions specified in the block diagrams' block(s) or operation(s). The program code instructions may be retrieved from a computer-readable storage medium and loaded into a computer, processor, or other programmable apparatus to configure the computer, processor, or other programmable apparatus to execute operations to be performed on or by the computer, processor, or other programmable apparatus. Retrieval, loading, and execution of the program code instructions may be performed sequentially such that one instruction is retrieved, loaded, and executed at a time. In some example embodiments, retrieval, loading and/or execution may be performed in parallel such that multiple instructions are retrieved, loaded, and/or executed together. Execution of the program code instructions may produce a computer-implemented process such that the instructions executed by the computer, processor, or other programmable apparatus provide operations for implementing the functions specified in the block diagrams' block(s) or operation(s).

Accordingly, execution of instructions associated with the blocks or operations of the block diagrams by a processor, or storage of instructions associated with the blocks or operations of the block diagrams in a computer-readable storage medium, supports combinations of operations for performing the specified functions. It will also be understood that one or more blocks or operations of the block diagrams, and combinations of blocks or operations in the block diagrams, may be implemented by special purpose hardware-based computer systems and/or processors which perform the specified functions, or combinations of special purpose hardware and program code instructions.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus comprising:
    a processor configured to receive a sample signal scan that includes a plurality of electromagnetic signal measurements at a discrete set of frequencies, each respective measurement having been taken by a spectrometer system passing an electromagnetic signal through a sample cell including a sample medium and a base medium,
    wherein the processor is configured to segment the sample signal scan into a plurality of frequency segments,
    wherein the processor is configured to process the sample signal scan segments to produce a respective plurality of corrected sample signal scan segments, wherein the processor being configured to process the sample signal scan segments includes, for each sample signal scan segment, being configured to:
        apply an inner-product operation on the sample signal scan segment and a respective set of eigenvectors from a plurality of sets of eigenvectors to generate a respective set of corresponding coefficients, the sets of eigenvectors having been generated by segmenting a plurality of background reference signal scans into a plurality of sets of background reference signal scan segments, and decomposing each set of background reference signal scan segments according to a singular value decomposition technique, each background reference signal scan including a plurality of electromagnetic signal measurements at a discrete set of frequencies, each respective measurement having been taken by the spectrometer system passing an electromagnetic signal through the sample cell including the base medium but without the sample medium, and
        subtract the sample signal scan segment from a linear combination of the respective set of eigenvectors and corresponding coefficients to thereby produce a respective corrected sample signal scan, and
    wherein the processor is configured to assemble the corrected sample signal scan segments.

2. The apparatus of claim 1, wherein the processor is further configured to receive and segment the plurality of background reference signal scans into a plurality of sets of background reference signal scan segments, and decompose each set of the background reference signal scan segments to generate the plurality of sets of eigenvectors.

3. The apparatus of claim 1, wherein the processor is further configured to identify an electromagnetic signal measurement in the sample signal scan corresponding to an electromagnetic signal measurement in the corrected sample signal that exceeds a specified absorption threshold,
    wherein the processor is configured to remove the identified electromagnetic signal measurement to produce a modified sample signal scan, and
    wherein the processor is configured to process the modified sample signal scan, including being configured to:
        apply an inner-product operation on the modified sample signal scan and each of a plurality of eigenvectors to generate a second plurality of corresponding coefficients, and
        subtract the sample signal scan from a linear combination of the eigenvectors and second plurality of corresponding coefficients to thereby produce a further corrected sample signal scan.

4. The apparatus of claim 1, wherein the processor is further configured to calculate a ratio of the sample signal scan to an average of the background reference signal scans, and adjust the corrected sample signal scan based on the ratio.

5. An apparatus comprising:
a processor configured to receive a sample signal scan that includes a plurality of electromagnetic signal measurements at a discrete set of frequencies, each respective measurement having been taken by a spectrometer system passing an electromagnetic signal through a sample cell including a sample medium and a base medium,
wherein the processor is configured to process the sample signal scan, including being configured to:
apply an inner-product operation on the sample signal scan and each of a plurality of eigenvectors to generate a plurality of corresponding coefficients, the plurality of eigenvectors having been generated by decomposing a plurality of background reference signal scans according to a singular value decomposition technique, each background reference signal scan including a plurality of electromagnetic signal measurements at a discrete set of frequencies, each respective measurement having been taken by the spectrometer system passing an electromagnetic signal through the sample cell including the base medium but without the sample medium, and
subtract the sample signal scan from a linear combination of the eigenvectors and corresponding coefficients to thereby produce a corrected sample signal scan,
wherein the processor is further configured to identify an electromagnetic signal measurement in the sample signal scan corresponding to an electromagnetic signal measurement in the corrected sample signal scan that exceeds a specified absorption threshold,
wherein the processor is configured to remove the identified electromagnetic signal measurement to produce a modified sample signal scan, and
wherein the processor is configured to process the modified sample signal scan, including being configured to:
apply an inner-product operation on the modified sample signal scan and each of a plurality of eigenvectors to generate a second plurality of corresponding coefficients, and
subtract the sample signal scan from a linear combination of the eigenvectors and second plurality of corresponding coefficients to thereby produce a further corrected sample signal scan.

6. The apparatus of claim 5, wherein the processor is further configured to calculate a ratio of the sample signal scan to an average of the background reference signal scans, and adjust the corrected sample signal scan based on the ratio.

7. A method comprising:
receiving a sample signal scan that includes a plurality of electromagnetic signal measurements at a discrete set of frequencies, each respective measurement having been taken by a spectrometer system passing an electromagnetic signal through a sample cell including a sample medium and a base medium;
segmenting the sample signal scan into a plurality of frequency segments;
processing the sample signal scan segments to produce a respective plurality of corrected sample signal scan segments, wherein processing the sample signal scan segment comprises, for each sample signal scan segment:
applying an inner-product operation on the sample signal scan segment and a respective set of eigenvectors from a plurality of sets of eigenvectors to generate a respective set of corresponding coefficients, the sets of eigenvectors having been generated by segmenting a plurality of background reference signal scans into a plurality of sets of background reference signal scan segments, and decomposing each set of background reference signal scan segments according to a singular value decomposition technique, each background reference signal scan including a plurality of electromagnetic signal measurements at a discrete set of frequencies, each respective measurement having been taken by the spectrometer system passing an electromagnetic signal through the sample cell including the base medium but without the sample medium; and
subtracting the sample signal scan segment from a linear combination of the respective set of eigenvectors and corresponding coefficients to thereby produce a respective corrected sample signal scan; and
assembling the corrected sample signal scan segments.

8. The method of claim 7 further comprising receiving and segmenting the plurality of background reference signal scans into a plurality of sets of background reference signal scan segments, and decomposing each set of the background reference signal scan segments to generate the plurality of sets of eigenvectors.

9. The method of claim 7 further comprising:
identifying an electromagnetic signal measurement in the sample signal scan corresponding to an electromagnetic signal measurement in the corrected sample signal scan that exceeds a specified absorption threshold;
removing the identified electromagnetic signal measurement to produce a modified sample signal scan; and
processing the modified sample signal scan, wherein processing the modified sample signal scan comprises:
applying an inner-product operation on the modified sample signal scan and each of a plurality of eigenvectors to generate a second plurality of corresponding coefficients, and
subtracting the sample signal scan from a linear combination of the eigenvectors and second plurality of corresponding coefficients to thereby produce a further corrected sample signal scan.

10. The method of claim 7 further comprising:
calculating a ratio of the sample signal scan to an average of the background reference signal scans; and
adjusting the corrected sample signal scan based on the ratio.

11. A method comprising:
receiving a sample signal scan that includes a plurality of electromagnetic signal measurements at a discrete set of frequencies, each respective measurement having been taken by a spectrometer system passing an electromagnetic signal through a sample cell including a sample medium and a base medium;
processing the sample signal scan, wherein processing the sample signal scan comprises:
applying an inner-product operation on the sample signal scan and each of a plurality of eigenvectors to generate a plurality of corresponding coefficients, the plurality of eigenvectors having been generated by decomposing a plurality of background reference signal scans according to a singular value decomposition technique, each background reference signal scan including a plurality of electromagnetic signal measurements at a discrete set of frequencies, each respective measurement having been taken by the spectrometer system passing an electromagnetic signal through the sample cell including the base medium but without the sample medium; and subtracting the sample signal scan from a linear combination of the eigenvectors and corresponding coefficients to thereby produce a corrected sample signal scan;

identifying an electromagnetic signal measurement in the sample signal scan corresponding to an electromagnetic signal measurement in the corrected sample signal scan that exceeds a specified absorption threshold;

removing the identified electromagnetic signal measurement to produce a modified sample signal scan; and processing the modified sample signal scan, wherein processing the modified sample signal scan comprises:

applying an inner-product operation on the modified sample signal scan and each of a plurality of eigenvectors to generate a second plurality of corresponding coefficients; and subtracting the sample signal scan from a linear combination of the eigenvectors and second plurality of corresponding coefficients to thereby produce a further corrected sample signal scan.

12. The method of claim 11 further comprising calculating a ratio of the sample signal scan to an average of the background reference signal scans, and adjusting the corrected sample signal scan based on the ratio.

13. A computer-readable storage medium having computer-readable program code portions stored therein, the computer-readable storage medium being non-transitory, the computer-readable program code portions being executable by a processor to cause an apparatus to perform one or more operations, the computer-readable program code portions comprising:

a first executable portion configured to receive a sample signal scan that includes a plurality of electromagnetic signal measurements at a discrete set of frequencies, each respective measurement having been taken by a spectrometer system passing an electromagnetic signal through a sample cell including a sample medium and a base medium; and a second executable portion configured to segment the sample signal scan into a plurality of frequency segments;

a third executable portion configured to process the sample signal scan segments to produce a respective plurality of corrected sample signal scan segments, wherein the third executable portion being configured to process the sample signal scan segments includes, for each sample signal scan segment, being configured to:

apply an inner-product operation on the sample signal scan segment and a respective set of eigenvectors from a plurality of sets of eigenvectors to generate a respective set of corresponding coefficients, the sets of eigenvectors having been generated by segmenting a plurality of background reference signal scans into a plurality of sets of background reference signal scan segments, and decomposing each set of background reference signal scan segments according to a singular value decomposition technique, each background reference signal scan including a plurality of electromagnetic signal measurements at a discrete set of frequencies, each respective measurement having been taken by the spectrometer system passing an electromagnetic signal through the sample cell including the base medium but without the sample medium, and subtract the sample signal scan segment from a linear combination of the respective set of eigenvectors and corresponding coefficients to thereby produce a respective corrected sample signal scan; and a fourth executable portion configured to assemble the corrected sample signal scan segments.

14. The computer-readable storage medium of claim 13, wherein the computer-readable program code portions further comprise:

a fifth executable portion configured to receive and segment the plurality of background reference signal scans into a plurality of sets of background reference signal scan segments; and a sixth executable portion configured to decompose each set of the background reference signal scan segments to generate the plurality of sets of eigenvectors.

15. The computer-readable storage medium of claim 13, wherein the computer-readable program code portions further comprise:

a fifth executable portion configured to identify an electromagnetic signal measurement in the sample signal scan corresponding to an electromagnetic signal measurement in the corrected sample signal scan that exceeds a specified absorption threshold;

a sixth executable portion configured to remove the identified electromagnetic signal measurement to produce a modified sample signal scan; and a seventh executable portion configured to process the modified sample signal scan, including being configured to:

apply an inner-product operation on the modified sample signal scan and each of a plurality of eigenvectors to generate a second plurality of corresponding coefficients, and subtract the sample signal scan from a linear combination of the eigenvectors and second plurality of corresponding coefficients to thereby produce a further corrected sample signal scan.

16. The computer-readable storage medium of claim 13, wherein the computer-readable program code portions further comprise:

a fifth executable portion configured to calculate a ratio of the sample signal scan to an average of the background reference signal scans; and a sixth executable portion configured to adjust the corrected sample signal scan based on the ratio.

17. A computer-readable storage medium having computer-readable program code portions stored therein, the computer-readable storage medium being non-transitory, the computer-readable program code portions being executable by a processor to cause an apparatus to perform one or more operations, the computer-readable program code portions comprising:

a first executable portion configured to receive a sample signal scan that includes a plurality of electromagnetic signal measurements at a discrete set of frequencies, each respective measurement having been taken by a spectrometer system passing an electromagnetic signal through a sample cell including a sample medium and a base medium;

a second executable portion configured to process the sample signal scan, including being configured to:

apply an inner-product operation on the sample signal scan and each of a plurality of eigenvectors to generate a plurality of corresponding coefficients, the plurality of eigenvectors having been generated by decomposing a plurality of background reference signal scans according to a singular value decomposition technique, each background reference signal scan including a plurality of electromagnetic signal measurements at a discrete set of frequencies, each respective measurement having been taken by the spectrometer system passing an electromagnetic signal through the sample cell including the base medium but without the sample medium, and subtract the sample signal scan from a linear combination of the eigenvectors and corresponding coefficients to thereby produce a corrected sample signal scan;

a third executable portion configured to identify an electromagnetic signal measurement in the sample signal scan corresponding to an electromagnetic signal measurement in the corrected sample signal scan that exceeds a specified absorption threshold;

a fourth executable portion configured to remove the identified electromagnetic signal measurement to produce a modified sample signal scan; and a fifth executable portion configured to process the modified sample signal scan, including being configured to:

apply an inner-product operation on the modified sample signal scan and each of a plurality of eigenvectors to generate a second plurality of corresponding coefficients, and subtract the sample signal scan from a linear combination of the eigenvectors and second plurality of corresponding coefficients to thereby produce a further corrected sample signal scan.

18. The computer-readable storage medium of claim 17, wherein the computer-readable program code portions further comprise a sixth executable portion configured to calculate a ratio of the sample signal scan to an average of the background reference signal scans, and adjust the corrected sample signal scan based on the ratio.

* * * * *